(12) United States Patent
Cornejo Cruz et al.

(10) Patent No.: US 8,065,017 B2
(45) Date of Patent: Nov. 22, 2011

(54) METHOD AND APPARATUS FOR OBTAINING AND REGISTERING AN ELECTRICAL COCHLEAR RESPONSE ("ECR")

(75) Inventors: Juan Manuel Cornejo Cruz, Del. Iztacalco (MX); Maria del Pilar Granados Trejo, Del. Iztacalco (MX)

(73) Assignee: Universidad Autonoma Metropolitana Unidad Iztapalapa, Mexico City (MX)

( * ) Notice: Subject to any disclaimer, the term of this patent is extended or adjusted under 35 U.S.C. 154(b) by 638 days.

(21) Appl. No.: 12/037,323

(22) Filed: Feb. 26, 2008

(65) Prior Publication Data

US 2008/0249589 A1 Oct. 9, 2008

Related U.S. Application Data

(60) Provisional application No. 60/891,582, filed on Feb. 26, 2007.

(51) Int. Cl.
*A61B 5/0484* (2006.01)
(52) U.S. Cl. .......................................... 607/57
(58) Field of Classification Search .............. 607/55–57; 600/559
See application file for complete search history.

(56) References Cited

U.S. PATENT DOCUMENTS

| | | | |
|---|---|---|---|
| 3,517,468 A * | 6/1970 | Woods | 52/79.1 |
| 4,400,590 A | 8/1983 | Michelson | |
| 5,626,629 A | 5/1997 | Faltys et al. | |
| 5,758,651 A | 6/1998 | Nygard et al. | |
| 5,999,856 A * | 12/1999 | Kennedy | 607/57 |
| 6,067,474 A | 5/2000 | Schulman et al. | |
| 6,157,861 A | 12/2000 | Faltys et al. | |
| 6,205,360 B1 | 3/2001 | Carter et al. | |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,751,505 B1 | 6/2004 | Van Den Honert et al. | |
| 6,915,166 B1 | 7/2005 | Stecker et al. | |
| 2007/0204694 A1 | 9/2007 | Davis | |
| 2007/0293785 A1 | 12/2007 | Litvak | |

OTHER PUBLICATIONS

Firszt, Jill B. et al., Neurophysiology of Cochlear Implant Users I: Effects of Stimulus Current Level and Electrode Site on the Electrical ABR, MLR, and N1-P2 Response Ear & Hearing, 2002, pp. 502-515, 0196/0202/02/2306-0502/0, Lippincott Williams & Wilkins, USA.

(Continued)

*Primary Examiner* — Scott Getzow
*Assistant Examiner* — Amanda Patton
(74) *Attorney, Agent, or Firm* — The Eclipse Group LLP (57) ABSTRACT

This invention relates to a method and apparatus for obtaining and registering the Electrical Cochlear Response ("ECR"). Particularly, the ECR refers to the electrical activity of the auditory nerve and the intracochlear residual tissue located in the neighborhood of an intracochlear stimulation electrode, when an external sound is presented to a Cochlear Implant user, human or animal. Applicants recognize that an ECR can be thought of as a far-field electrical potential registered on the scalp of an implanted patient. Applicants, through their method and apparatus, can extract that potential from the patient's spontaneous electroencephalographic activity (EEG) and measure it by using an averaging algorithm. The Electrical Cochlear Response can be applied for adaptation, calibration, performance evaluation and failure detection of the Cochlear Implant of the implanted patient. Also Applicants' method can be applied to estimate the audiometric thresholds of the Cochlear Implant even without the implanted patient's knowledge.

14 Claims, 11 Drawing Sheets

OTHER PUBLICATIONS

Geier, Lisa L. et al., The Effects of Limiting the Number of Nucleus 22 Cochlear Implant Electrodes Programmed on Speech Perception, Ear and Hearing, 1992, pp. 340-348, vol. 13, No. 5, Williams & Wilkins, USA.

Gordon, Karen A. et al., Toward a Battery of Behavioral and Objective Measures to Achieve Optimal Cochlear Implant Stimulation Levels in Children, Ear & Hearing, 2004, pp. 447-463, 0196/0202/04/2505-0447/0, Lippincott Williams & Wilkins, USA.

Hughes, Michelle L. et al., A Longitudinal Study of Electrode Impedance, the Electrically Evoked Compound Action Potential, and Behavioral Measures in Nucleus 24 Cochlear Implant Users, Ear & Healing, 2001, pp. 471-486, 0196/0202/01/2206-0471/0, Lippincott Williams & Wilkins, USA.

Mahoney, Mary Jane et al., The User of Averaged Electrode Voltages to Assess the Funtion of Nucleus Internal Cochlear Implant Devices in Children, Ear & Healing, 1994, pp. 177-183, 0196/0202/94/1502-0177$3.00/0, Williams & Wilkins, USA.

PCT International Search Report and Written Opinion, International Application No. PCT/MX 08/00151 mailed Apr. 17, 2009.

\* cited by examiner

METHOD AND APPARATUS FOR OBTAINING AND REGISTERING AN ELECTRICAL COCHLEAR RESPONSE ("ECR")

RELATED APPLICATION

This Utility Patent Application is based upon an earlier Provisional Patent Application Ser. No. 60/891,582, filed Feb. 26, 2007. Applicants claim the benefit of priority from the Provisional Application.

FIELD OF THE INVENTION

The present invention relates, in general, to Cochlear Stimulation Systems. More particularly, it relates to methods and apparatuses for obtaining an Electrical Cochlear Response ("ECR").

BACKGROUND OF THE INVENTION

Hearing loss is generally classified in two types: conductive and sensorineural. Conductive hearing loss is result of a decreasing of the mechanical chain functionality constituted by the external and middle ear, which captures and drives the mechanical energy of the sound to the cochlea. Sensorineural hearing loss is due to the deficiency or damage of the hair cells in the cochlea. Those hair cells are needed to codify the sound into nerve impulses sent to the brain.

While a conductive hearing loss can often be corrected, at least partially by medical or surgical procedures or by using conventional auditory prosthesis that amplifies the sound. To compensate sensorineural hearing loss, many Cochlear Stimulation Systems have been developed, such as the ones described in U.S. Pat. No. 4,400,590 to Michelson, U.S. Pat. No. 5,626,629 A to Faltys et al., U.S. Pat. No. 6,067,474 to Schulman et al., U.S. Pat. No. 6,157,861 A to Faltys et al., U.S. Pat. No. 6,219,580 B1 to Faltys et al., U.S. Pat. No. 6,249,704 B1 to Maltan et al., and U.S. Pat. No. 6,289,247 B1 to Faltys et al. To overcome sensorineural deafness, those systems bypass the hair cells function by means of the direct electrical stimulation of the auditory nerve fibers to create a sound perception in the implanted patient's brain. In most of these systems, electrical stimulation is made through an intracochlear electrode array excited by a suitable external electrical power source.

Previous to the electrical stimulation, each of these Cochlear Stimulation Systems processes the spectrum of frequencies of the input sound. This spectrum is separated into a certain number of frequency bands by using a band-pass filters bank. After this, the amplitude of the output signal of each filter is translated or mapped based on: loudness perceptions criteria of the patient implanted with a Cochlear Stimulation System; and an electrical stimulation current level for each one of the intracochlear electrodes.

Throughout the remainder of this application, including the appended Claims, the term "implanted patient" is used to refer to a patient implanted with a Cochlear Stimulation System.

Some of the algorithms used to translate the input sound into an electrical stimulation current are described in U.S. Pat. No. 3,751,605 to Michelson, U.S. Pat. No. 4,267,410 to Forster et al., U.S. Pat. No. 4,284,856 to Hochmair et al., U.S. Pat. No. 4,400,590 to Michelson, U.S. Pat. No. 4,408,608 to Daly et al., U.S. Pat. No. 4,428,377 to Zollner et al. and U.S. Pat. No. 4,532,930 to Crosby et al. There are operation parameters of the Cochlear Stimulation Systems, which take part in the dynamic range mapping of the input sound into an adequate dynamic range of the electrical stimulation current. The residual cochlear tissue condition and the loudness sensations parameters of the implanted patient are some other parameters taking part too.

Among these parameters are some that refer to the signal processing that the particular Cochlear Stimulation System makes over the input sound and those relative to the electrical stimulation current. There are numerous parameters, such as: the number of channels or frequency bands in which the input sound is separated; microphone signal bandwidth; sound processor sensibility; automatic gain control attack and releasing time; the compression relation of the input sound; the intracochlear electrode associated to each frequency band; and the electrical stimulation current dynamic range for each intracochlear electrode. These parameters, which also include the corresponding stimulation strategy (i.e., SPEAK, ACE, CIS or SAS), are selected to convert the input sound into an electrical stimuli applied to the intra cochlear electrode such as: repetition rate of the biphasic pulse of electrical current; width of the pulse for each channel; elapsed time between positive and negative phases of this pulse (GAP); and the number of maximum spectral peaks periodically chosen for its presentation. The operation of the Cochlear Stimulation System must be adjusted according to the individual needs of the implanted patient to accomplish the greatest benefit as possible. For a particular patient and Cochlear Stimulation System there exist optimal stimulation current set values so that the sound can be intelligible, without being painfully sonorous or as soft as undetectable.

The task for the expert clinician is to find the best set of stimulation parameter values or "MAP" to fulfill the patient needs and that offers the best possible performance of the device. The Cochlear Stimulation System fitting poses some inconvenience if there is not any quantifiable parameter; the construction of this MAP based on the subjective judgment of the implanted subject becomes, in some way, a successive approximation procedure. The determination of this MAP based on some prescribed method that employs a limited number of measures has not proved to be successful in all the implanted patients. Besides, it is not possible to adjust each stimulation parameter value one at the time because most of them interact with each other. For example, the number of functional intracoclear electrodes and the biphasic pulse width of the stimulation electrical current limit the stimulation speed for the intracochlear electrodes.

For these reasons, there are different approaches to this problem in clinical practice. Some professionals use the set values suggested by the manufacturer or some other maps of their own. Others attempt to adjust stimulation parameters on individual electrodes based on psychophysical measures and interpolating these values to the neighbors to adjust the total of the electrodes. The problem still remains the same, nowadays there is no known method for the systematic identification of the optimal MAP for a particular user. Most of the actual methods are difficult to apply on the implanted subject, take too much time, and they are poorly reliable.

Alternative to psychophysical methods are those that use the stapedius reflex (SR), the middle ear response (MER), or the evoked compound action potential (ECAP), as an objective measure of the physiological response to sound. Such methods are disclosed in U.S. Pat. No. 5,626,629 A to Faltys et al., U.S. Pat. No. 6,157,861 A to Faltys et al., U.S. Pat. No. 6,289,247 B1 to Faltys et al., U.S. Pat. No. 6,205,360 B1 to Carter et al., U.S. Pat. No. 6,415,185 B1 to Maltan, U.S. Pat. No. 6,751,505 B1 to Van Den Honert et al., U.S. Pat. No. 6,915,166 to Stecker et al., U.S. Pat. No. 7,043,303 B1 to Overstreet, U.S. Pat. No. 7,076,308 B1 to Overstreet et al. and U.S. Pat. No. 7,107,101 B1 to Faltys.

The example of U.S. Pat. No. 6,157,861 A involves a Cochlear Stimulation System and a fitting method. An electrical stimulation is applied to the intracochlear electrodes, and the middle ear reflex (MER) is measured as a response.

Another example is described in U.S. Pat. No. 6,915,166, where an improved method for intracochlear electrodes selection in a Cochlear Stimulation System is disclosed. While variable intensity electrical stimuli are presented to each intracochlear electrode, evoked compound action potential (ECAP) through an implanted electrode is measured. This and other similar methods offer the possibility to estimate the stimulation electrical current minimum and maximum psychophysical values.

The minimal value or threshold level "T" is the electrical current level which, when applied to the corresponding electrode in a certain frequency band, produces a sound perception sensation in, at least fifty percent (50%) of the cases. The maximum value of this current or comfort level "C" corresponds to a moderately sound perception, without being uncomfortable. Nevertheless threshold and comfort levels might not match with the psychophysical levels when complex sounds or live voice is presented.

It is well known that there is an individual overestimation of the psychophysical levels for intracochlear electrodes when using complex sounds or live voice as a sound stimulus. Overestimating the extremes values of the electrical current level dynamic range reduces the benefit of the Cochlear Stimulation System, especially in noisy environment.

The mentioned tests could be done during or after the implant surgery. However, ideal test conditions are with the implanted patient under sedation. Stimulation with variable intensity current pulses might cause patient annoyance, or even painful sensations, when the patient is awake and alert. The right programming of the Cochlear Stimulation System is particularly difficult; yet most previous adjustments considered to be accurate or suitable have been determined based on feedback expressed by the implanted patient. Suitable adjustments might not occur as the patient feedback is subjective.

Users of the same Cochlear Stimulation System could have different performance in sound and speech perception, due to factors such as non-homogeneous distribution of the residual auditory nerve fibers along the cochlea and the electrical impedance characteristics between auditory nervous fibers and intracochlear electrodes. The patient's restricted communications skills to inform the professional clinician about the quality of his sound perception, contributes to the wide performance variation among users of a same Cochlear Stimulation System, standard free field audiometry is not reliable for children under three years old.

Most objective methods take advantage of the facilities included in a Cochlear Stimulation System, which allow the direct electric stimulation through a pair of intracochlear electrodes and then pick up a signal related to the physiological response of the auditory nerve system. For this purpose, it is necessary that the Cochlear Stimulation System possesses reception and transmission information capabilities to and from external environment for accepting the electrical code stimulation for the intracochlear electrodes and sending back the corresponding response. See the example described in U.S. Pat. No. 5,758,651 issued to Nygard et al. However, Cochlear Stimulation Systems without such facilities, and the lack of hardware compatibility between systems made by different manufacturers, do not allow a generalized use of these tests.

Excluding the role of the speech processor from the system fitting procedure does not assure adequate sound perception in the implanted patient under sound or speech environment. This is because the intracochlear electrodes electrical stimulation current dynamic range, established by means of any of the objective methods known up to now, might not correspond to the dynamic range of the implanted subject sound perception.

It is well known that excitation, by electrical current of different sites along the cochlea, is translated by the brain into a pitch perception that goes from high to low as stimulation moves from base to apex. Nevertheless, a loudness sensation can not be clearly established in the implanted patient because it depends on the local characteristics of the residual cochlear tissue in the vicinity of the stimulation electrode. That is why two contiguous intracochlear electrodes with the same electrical stimulation dynamic range might correspond with an adequate loudness sensation in one case and yet be uncomfortably painful in the other. Once the electrical stimulation dynamic range for the electrodes array has been established, the patient's perception of loudness depends on the residual cochlear tissue properties in the electrode neighborhood and the Speech Processor operation parameters, specifically on the sensitivity and gain. In short, the loudness perception of the implanted patient results from the combined effect of the residual cochlear tissue excitability properties, the stimulation electrical current dynamic range and the speech processor amplifying characteristics. Applicants have determined that the implanted patient's loudness perception is related to the Electrical Cochlear Response and the measurement of some of its parameters.

Accordingly, it is a primary object of the present invention to provide an apparatus and objective method which through the presentation of an external sound stimuli of variable intensity, duration and frequency, and measuring the Electrical Cochlear Response, determine the stimulation electrical current dynamic range for the intracochlear electrode array through a patient's "T" and "C" psychophysical levels estimation; all this without the conscious participation of the implanted patient.

It is a more specific object to provide a unique apparatus and method to evaluate Cochlear Stimulation System performance, to estimate audiometric threshold, and to detect nonfunctional intracochlear electrodes.

It is another specific object, commensurate with the above-listed objects, to provide an apparatus and methodology suitable for either a pediatric or adult cochlear implant user no matter if the Cochlear Stimulation System possesses bidirectional data transmission facilities to the external environment.

SUMMARY OF THE INVENTION

The present invention provides a method and apparatus for obtaining the Electrical Cochlear Response ("ECR"), which is related with the implanted user's sound perception. ECR is the electrical potential or voltage due to electrical current passing through intracochlear residual tissue located between an active and a reference electrode of a Cochlear Stimulation System.

By establishing the relationship between an external sound and the corresponding ECR measured parameters, this invention permits an objective estimation of the electrical current dynamic range for each one of the Cochlear Stimulation System's intracochlear electrodes, which assures proper sound perception for the implanted user.

The ECR is obtained through the presentation of external variable duration, intensity and frequency sound stimuli while the Cochlear Stimulation System is running for an initial set of its operation parameters. Through averaging of a convenient number of spontaneous implanted user's EEG epochs picked up every time an external sound stimulation is presented, ECR is obtained for each intracochlear electrode. Once obtained, the ECR is measured to determine a set of its parameters such as amplitude, phase, latency, morphology and amplitude growing function. A pattern recognition system analyses these parameters to carry out different aspects of the present invention.

Some aspects of the present invention provide methods for "Fitting," "Calibration," "Performance Evaluation and Failure Detection," and "Audiometric Thresholds Estimation" of the implanted patient.

BRIEF DESCRIPTION OF THE DRAWINGS

The above and other objects of this invention will become more readily apparent upon reading the following text and drawings, in which.

DETAILED DESCRIPTION OF THE PREFERRED EMBODIMENTS

Measuring different parameters of the electrical activity generated by the intracochlear electrode surrounding cochlear structures, due to an electrical stimulation, provides information of the residual cochlear tissue behavior. Knowing this behavior makes it possible to adjust part or all of the operation parameters set values of a Cochlear Stimulation System, according to the particular needs of an implanted patient. An Electrical Cochlear Response ("ECR") is present every time the implanted patient's Cochlear Stimulation System processes an external environmental sound. ECR is an essential element for in situ evaluation of the system.

Figure 1A:
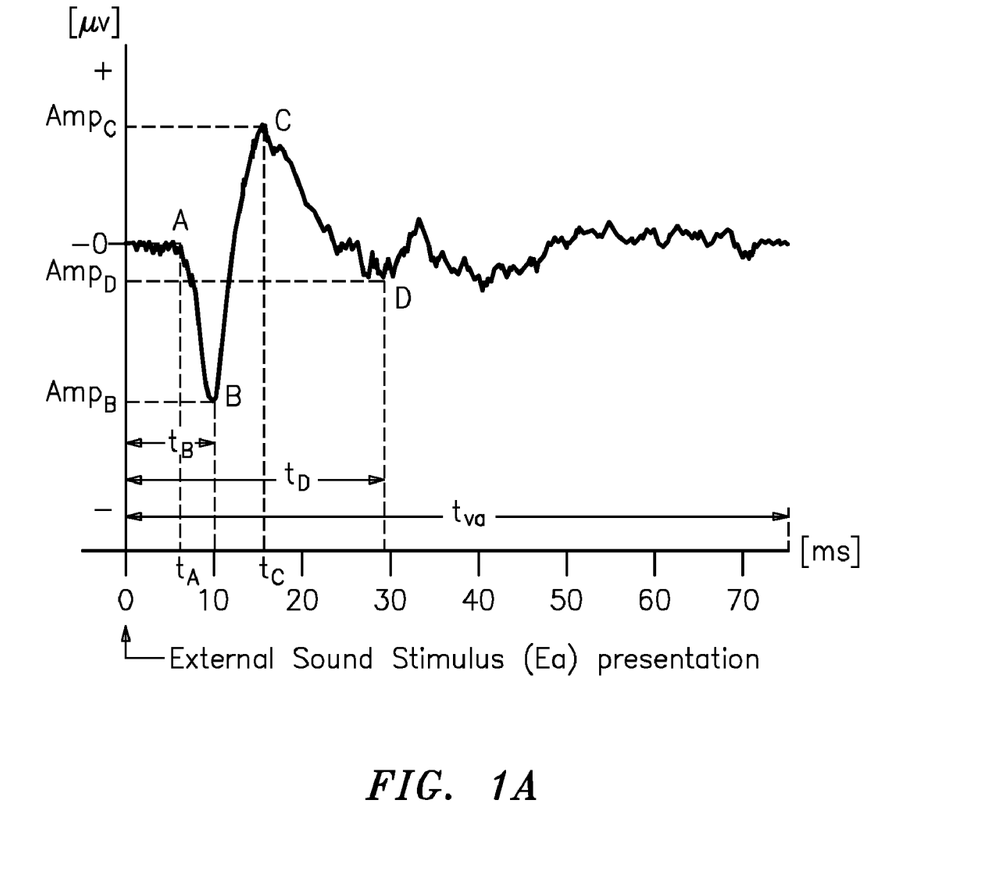
FIG. 1A depicts a typical ECR waveform.
Figure 1B:
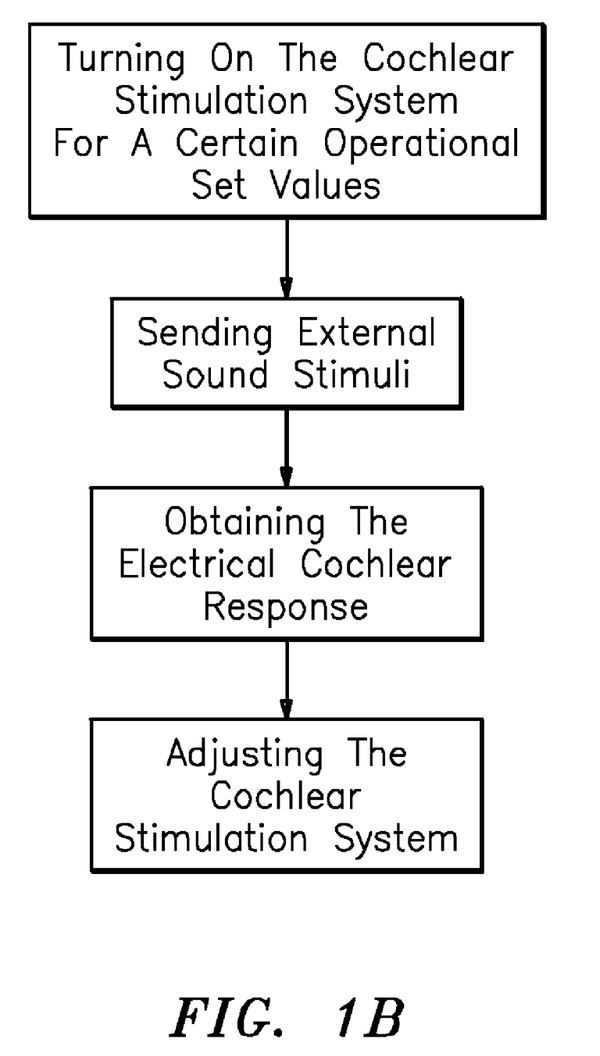
FIG. 1B depicts a simplified flowchart of Applicants' procedure, to achieve a proper Cochlear Stimulation System fitting according to this invention.

FIG. 1 shows the ECR. This response is an electrical potential due to electrical current passing through a pair of intracochlear electrodes whenever a patient's implanted Cochlear Stimulation System processes an environmental sound; it also shows the ECR's characteristic parameters that describe a time varying electric potential waveform. In Applicants' disclosed apparatus and method, such waveform is picked up by using scalp electrodes regardless of whether the implanted patient's Cochlear Stimulation System possesses bidirectional data transmission facilities. Among others, this far-field electric potential receives contributions from auditory nerve fibers activity, cochlear nucleus and residual cochlear tissue in the intracochlear electrode vicinity.

Interesting properties of the ECR activity peaks can be grouped in temporal (latency and time course), spatial (morphology, amplitude and phase) and frequency. These properties and their relationships, depend on a variety of factors such as: skin-scalp electrode impedance; relative position of scalp electrodes regarding intracochlear stimulation electrodes; impedance value between intracochlear electrodes and residual cochlear tissue; stimulation electric pulse width; repetition rate; electrical stimulation current level; and intensity level and frequency of the external sound stimulus.

Changes in the ECR's waveform morphology and its peaks time relationship might be possible because of: electrodes array depth insertion; pathological condition of the residual cochlear tissue, residual neuronal density and integrity; underlying neural synchrony; and external sound stimulation frequency, intensity level and timing features as well. Generally individual ECR waveforms comprise a negative potential peak B sometimes followed by a positive potential peak C, followed by a negative potential peak D, and going back along a basal line approximately to zero potential value. Amplitude and time relationship of this peaks are labeled as $Amp_B$, $Amp_C$, $Amp_D$ and $t_B$, $t_C$, $t_D$ respectively, as shown in FIG. 1. ECR is obtained once the Cochlear Stimulation System sound processor senses and processes an external input sound followed by the resulting scalp electric potential measurement. Generally external sound stimulation comprises a sound series of variable duration, intensity and frequency apart from each other by a time interval. ECR might comprise an electric potential waveform series generated by intracochlear structures located in the neighborhood of the stimulation intracochlear electrode.

In FIG. 1 the Y-axis or amplitude is measured in micro volts ("μV") and the X-axis is the time window duration measured in milliseconds ("ms"). Also: A=ECR starting point; B=minimum negative peak following A; C=maximum positive peak following B; D=minimum negative peak following C; $t_A$=elapsed time for starting point A; $t_B$=elapsed time for negative peak B; $t_C$=elapsed time for positive peak C; $t_D$=elapsed time for negative peak D; $t_{va}$=analysis window; $Amp_B$=peak B amplitude; $Amp_C$=peak C amplitude; and $Amp_D$=peak D amplitude.

The present invention discloses a method and apparatus which, through a relationship between ECR and external sound stimulus parameters, allow a clinician to know the intracochlear electrode array performance without the conscious implanted patient's participation.

Figure 2:
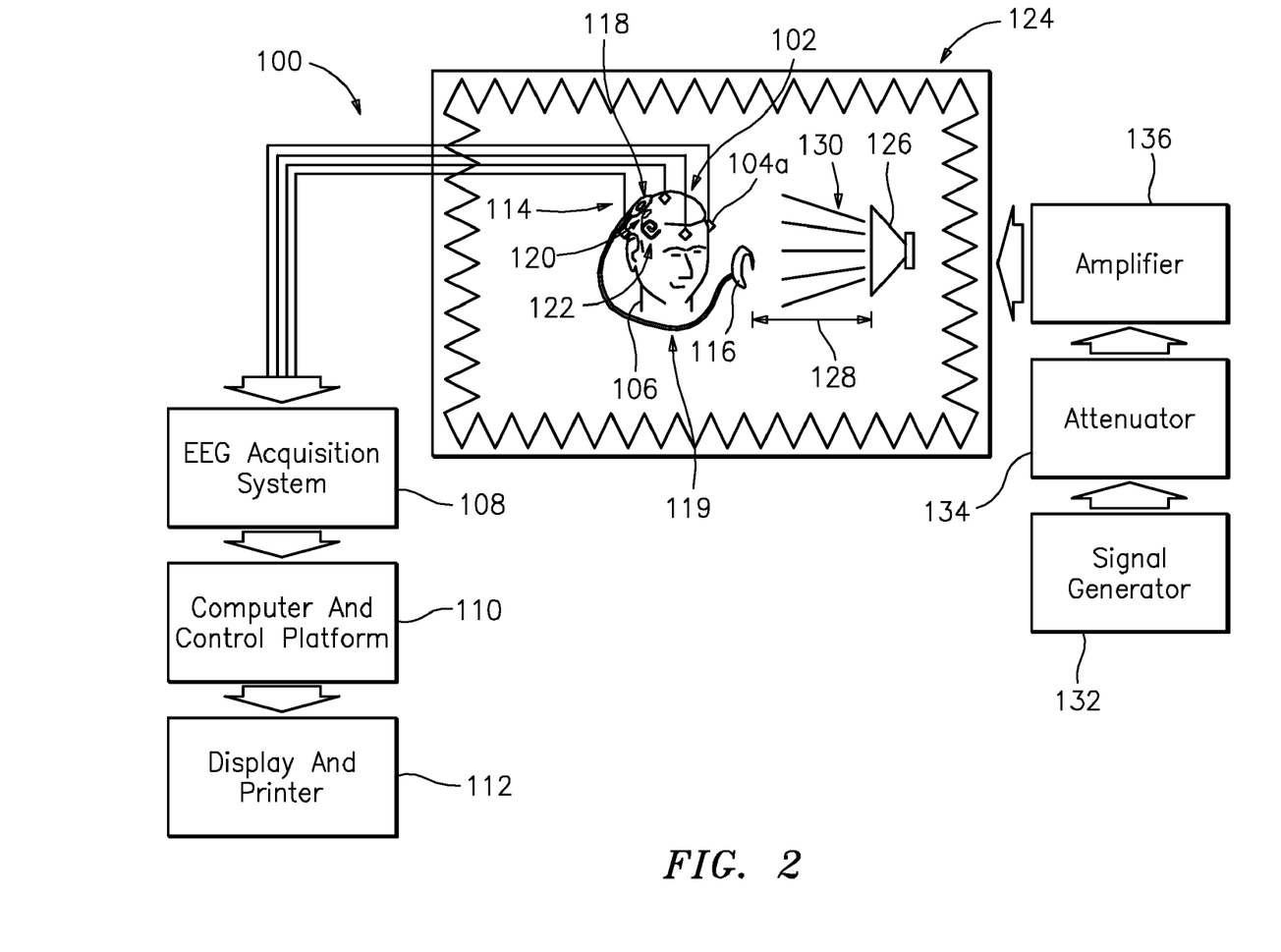
FIG. 2 shows a preferred embodiment of Applicants' unique apparatus for registering and measuring the implanted patient's Electrical Cochlear Response (ECR) in a sound field environment, wherein the sound field is calibrated.

FIG. 2 shows Applicants' preferred apparatus 100 set up to carry out Applicants' methodology for registering and measuring the Electrical Cochlear Response (ECR) of an implanted patient through an external sound stimulus presentation in a sound field environment. The apparatus 100 set-up comprises: a register electrodes system 102, used for picking up the implanted patient's EEG activity, preferably has four EEG or "scalp" electrodes (e.g., 104a) placed on the scalp of the implanted patient 106; the register electrode system 102, through the scalp electrodes (e.g., 104a), is connected to the input of an EEG acquisition system 108; output data of this EEG acquisition system 108 is sent in a conventional way (e.g., cable or wireless) to the computer and control platform 110 (described below) which accomplishes control, storage, calculus and information reports functions; a display and printer 112 for the reports; and a standard Cochlear Stimulation System 114 comprised of external and internal parts.

External parts include a sound processor 116 (e.g., Cochlear Corporation, Englewood, Colo., U.S.A.; ESPrit 3G Speech Processor) and a reception/transmission antenna 118 connected to the sound processor 116 by connection cable 119. Internal parts include the cochlear implant 120 (e.g., Cochlear Corporation, Englewood, Colo., U.S.A.; Nucleus C124M Cochlear Implant) and an intracochlear electrode array 122 (e.g., Cochlear Corporation, Englewood, Colo., U.S.A.; Contour Advance Electrode).

The intracochlear electrode array 122 of intracochlear electrodes is implanted inside the patient's cochlea (i.e., inner part of the ear). This array is part of the Cochlear Stimulation System 114; whenever a pair (i.e., active and reference electrodes) of intracochlear electrodes is activated an electrical current is delivered to the patient's auditory nerve. Surface (scalp) electrical potential or voltage developed due to this electrical current is picked up by Applicant's method and apparatus via the EEG electrodes (e.g., 104a).

A sedated or asleep patient 106 is led or placed into an audiometric enclosure 124. The patient, while wearing Cochlear Stimulation System 114, is positioned in front of an electroacoustic transducer or audio speaker 126, with the speaker 126 facing the sound processor's 116 microphone a short distance (e.g., 128) away.

The audiometric enclosure 124 allows a sound field 130 to be calibrated inside it and an environmentally low noise level, at least between the speaker 126 and the sound processor's 116 microphone (worn by the patient).

External sound stimulus is constructed by a dedicated system preferably comprising: a signal generator 132, an attenuator 134, and an amplifier 136 connected (e.g., by cables or wireless) to the electroacoustic transducer or speaker 126. Signal generator 132 determines wave shape and frequency and attenuator 134 rules the amplitude of the stimulation signal. The strength of this signal is increased by the amplifier 136 to achieve the intensity sound required by the test. Finally this amplified signal is presented to the patient 106 through an electroacoustic transducer or speaker 126. Speaker 126, in turn, transmits external sound stimuli along distance 128 to the sound processor's 116 microphone.

Sound field 130 must be calibrated to fulfill frequency range, low noise, and intensity level requirements for the distance 128 in such a way that external sound stimuli are suitable and safe for the patient.

By means of this apparatus 100 and using digital signal processing algorithms such as analog, digital or adaptive filtering, noise reduction or any other similar method to improve signal-to-noise ratio, ECR might be obtained from registered EEG epochs time locked with external sound stimulus presentation.

Once ECR is obtained, it is processed by the computer and control platform 110. The computer and control platform 110 can be any suitable averaging system employing a computer and software with a pattern recognition algorithm. Alternatively, it can be an appropriately programmed general-purpose computer, or a dedicated analog and/or digital device, both of which are well known to those of ordinary skill in the art.

Figure 3:
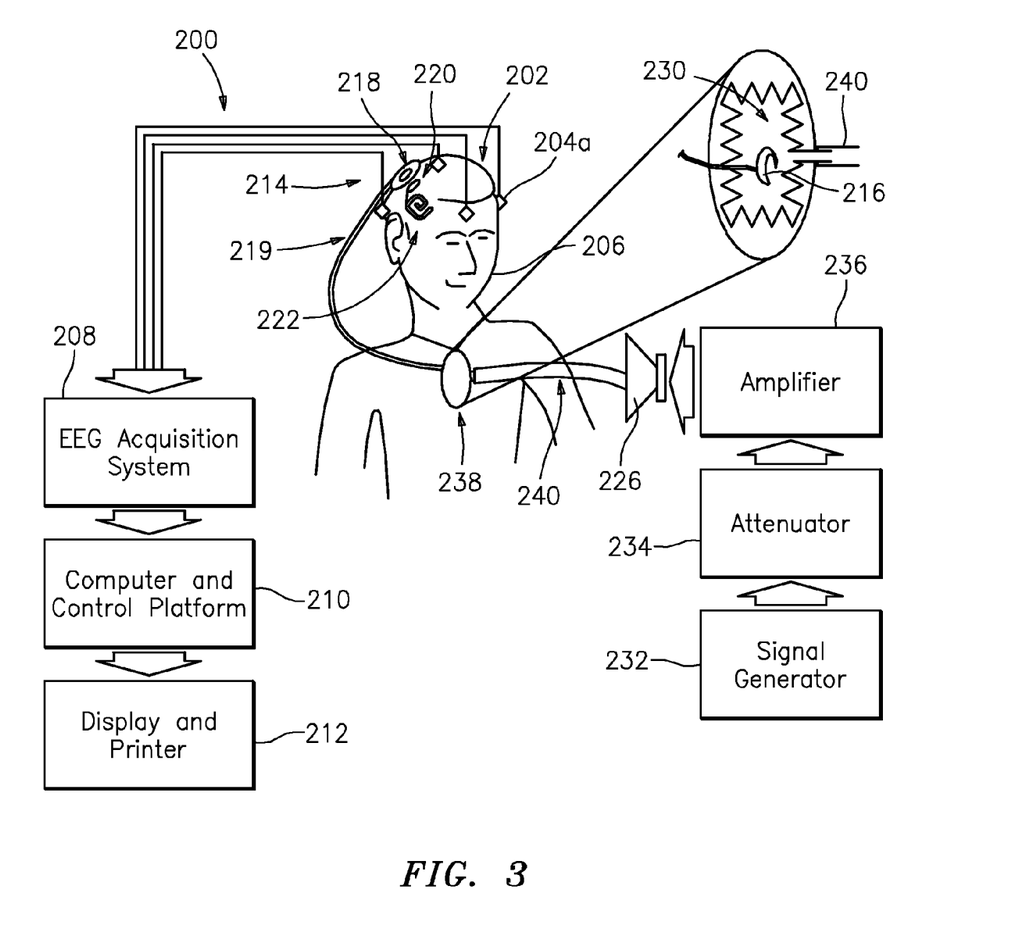
FIG. 3 shows another embodiment of Applicants' apparatus.

FIG. 3 includes several items (i.e., structural elements) found in FIG. 2. Like parts in FIG. 3 are given the same reference numbers, but with the prefix 200 instead of 100. For example, the cochlear implant is labeled 220 in FIG. 3.

A variation 200 (see FIG. 3) of the previous set-up 100 of FIG. 2 is to locate the sound processor's 216 microphone inside a test sound chamber 238 of reduced dimensions; in other words, a small container. In this set-up 200, sound from speaker 226 is mechanically coupled to the "reduced dimensions" test sound chamber 238 by means of a flexible tube 240. The sound field 230 inside chamber 238 is calibrated to meet the same quality requirements as in the external sound field 130.

Prior to a stimuli presentation, the register electrodes system (102, 202), placed on the implanted patient (106, 206), is connected to an input of the EEG acquisition system 208. The sound stimuli presented by the electroacoustical transducer 226 are composed of a plurality of variable intensity and frequency short time stimuli. Frequencies included in these sound stimuli are those corresponding to each intracochlear electrode of the intracochlear electrode array (e.g., 222) according to the patient's frequency band mapping assignment. See, e.g., FIG. 10.

Sound stimulus for a given frequency and intensity is presented in a repetitive way. Along with every sound stimulus presentation an EEG epoch is picked up and, after passing an artifact rejection criterion, is included in the averaging procedure. ECR for a given frequency and intensity sound stimuli is obtained through the corresponding EEG epochs averaging. See FIG. 8. ECR identification is made by a pattern recognition system. The pattern recognition system determines ECR presence by using criteria such as EEG epoch averaging waveform comparison with a target template, ECR amplitude threshold value, signal-to-noise ratio value, data statistical behavior or through out searching and measuring activity peaks in a time window suitable to intensity and frequency of the external sound stimulus. See FIG. 1.

Based on the ECR parameters measurement, the present invention provides a method that optimizes and facilitates the fitting of the Cochlear Stimulation System (114, 214). A secure, comfortable and suitable electrical current stimulation for the implanted patient (106, 206) is assured according to the parameters of time length, intensity level and frequency of an external sound stimulation.

The inventive subject matter solves a number of problems. First, it removes the clinician from the process of fitting a Cochlear Stimulation System (114, 214) based on a patient's perceptual information alone. Second, the use of a sound stimulation, which takes into account the role of the sound processor of the Cochlear Stimulation System (114, 214) in the stimulation chain, allows a fitting procedure that resembles the standard sound external environment. Third, the fitting procedure by itself is more kind and comfortable for the clinician and the patient (106, 206) because the patient is asleep or under sedation. Fourth, the possibility for under or over electrical current stimulation is reduced. Fifth, the conscious cooperation of the patient is not necessary. Sixth, this methodology application does not depend on Cochlear Stimulation System (114, 214) external environment bidirectional data transmission facilities, so it might be used with any current Cochlear Stimulation System.

In one aspect, the inventive subject matter relates to a method for fitting an implanted patient's Cochlear Stimulation System (114, 214), broadly comprising the steps of: (a)

turning on the Cochlear Stimulation System (114, 214) for an initial operational parameter values (i.e., the number of channels or frequency bands in which the input sound is separated; sound processor gain and sensibility; the intracochlear electrode associated to each frequency band and the electrical stimulation current dynamic range for each intracochlear electrode); (b) presenting external sound stimuli by, e.g., electro acoustical transducer 126, 226; (c) obtaining and measuring the ECR; (d) adjusting the Cochlear Stimulation System (114, 214) to obtain the ECR on the intracochlear electrode array (e.g., 122, 222) for a certain external sound intensity; (e) setting the dynamic range of the electrical stimulation current level for the intracochlear electrodes; and (f) reporting the operational parameters of the intracochlear electrodes.

In a second aspect, the inventive subject matter relates to a method for calibrating an implanted patient's Cochlear Stimulation System (114, 214), broadly comprising the steps of: (a) turning on the Cochlear Stimulation System (114, 214) with the typical operational parameters set (i.e., the number of channels or frequency bands in which the input sound is separated; sound processor gain and sensibility; the intracochlear electrode associated to each frequency band and the electrical stimulation current dynamic range for each intracochlear electrode) used by the implanted patient (106, 206) under daily conditions; (b) presenting external sound stimuli (e.g., by electro acoustical transducer 126, 226) within a suitable and comfortable dynamic range; (c) obtaining and measuring the ECR; and (d) adjusting the dynamic range of the electrical stimulation current level for the intracochlear electrode array (e.g., 122, 222) according to the ECR parameters.

In a third aspect, the inventive subject matter relates to a method for performance evaluation and failure detection of an implanted patient's Cochlear Stimulation System (114, 214), broadly comprising the steps of: (a) turning on the Cochlear Stimulation System (114, 214) with the typical operational parameters set (i.e., the number of channels or frequency bands in which the input sound is separated; sound processor gain and sensibility; the intracochlear electrode associated to each frequency band and the electrical stimulation current dynamic range for each intracochlear electrode) used by the implanted patient (106, 206) under daily conditions; (b) measuring Cochlear Stimulation System (114, 214) noise level from its operation without any external sound input; (c) presenting external sound stimuli (e.g., by electro acoustical transducer 126, 226) within a suitable and comfortable dynamic range; (d) obtaining and storing (i.e., registering) of the ECR's measured parameters; and (e) reporting noise levels, non-functional intracochlear electrodes and Cochlear Stimulation System (114, 214) performance, based on ECR parameter values.

Additionally, the inventive subject matter relates, in a fourth aspect, to a method for audiometric threshold estimation of an implanted patient. This is done considering the minimum external sound intensity necessary for an ECR detection in the corresponding electrode of the intracochlear electrode array (e.g., 122, 222), broadly comprising the steps of: (a) turning on the Cochlear Stimulation System (114, 214) with the typical operational parameters set (i.e., the number of channels or frequency bands in which the input sound is separated; sound processor gain and sensibility; the intracochlear electrode associated to each frequency band and the electrical stimulation current dynamic range for each intracochlear electrode) used by the implanted patient under daily conditions; (b) presenting external sound stimuli (e.g., by electro acoustical transducer 126, 226) within a suitable and comfortable dynamic range; (c) obtaining and measuring the ECR; and (d) estimating audiometric thresholds based on the minimum external sound intensity necessary for ECR detection in the corresponding electrode of the intracochlear electrode array (e.g., 122, 222).

Applicants have included several drawings (FIGS. 4-7), including flowcharts, to help describe how to carry out their preferred method while using the above-identified apparatus set-ups 100, 200.

Figure 4:
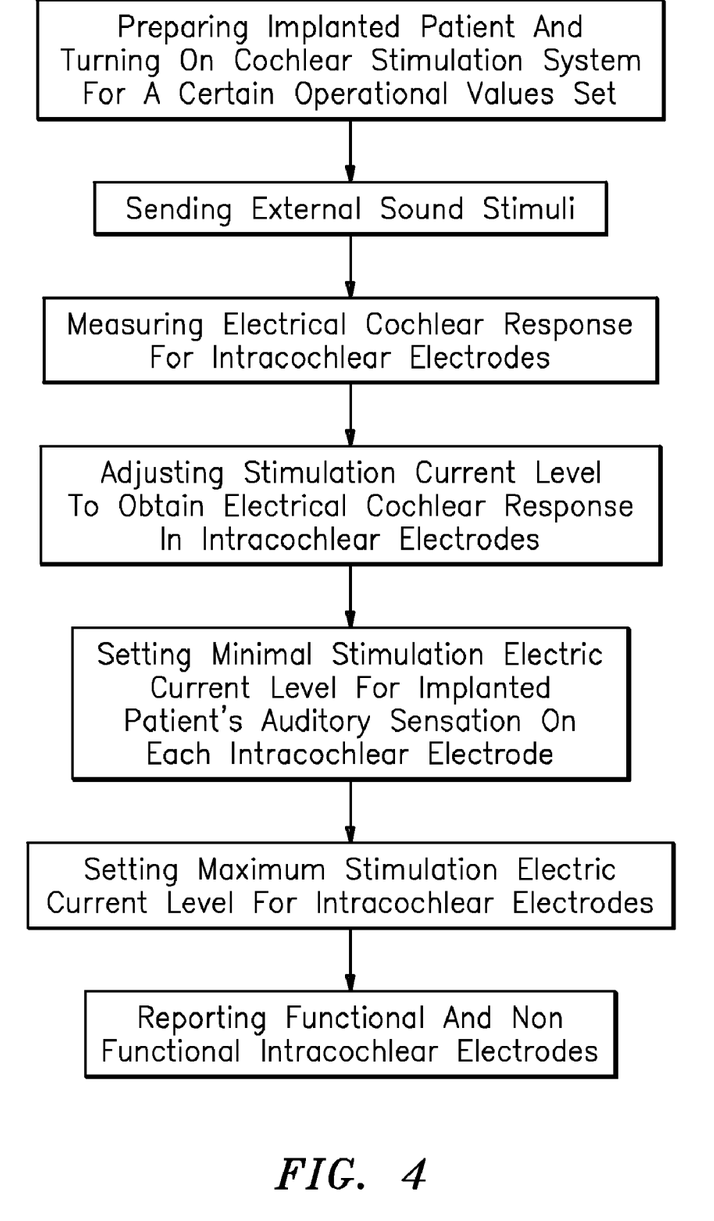
FIG. 4 shows a flowchart depicting the steps traversed to fit the implanted patient's Cochlear Stimulation System, according to the present invention.

FIG. 4 is a flowchart depicting a preferred method for fitting a Cochlear Stimulation System (e.g., 114, 214) based on the measure of the Electrical Cochlear Response, according to the present invention. The preferred "fitting" method steps comprise: (a) preparing an implanted patient (e.g., 106, 206) by placing Register Electrode System 102, 202 on the scalp and turning on the Cochlear Stimulation System (e.g., 114, 214) for an initial operational parameter values set (i.e., the number of channels or frequency bands in which the input sound is separated; sound processor gain and sensibility; the intracochlear electrode associated to each frequency band and the electrical stimulation current dynamic range for each intracochlear electrode) previously determined by the clinician; (b) presenting external sound stimuli of variable duration, intensity level and frequency delivered by an electro acoustic transducer 126, 226; (c) picking up an EEG epoch with the presentation of each sound stimulus of a given frequency and intensity level, by using an averaging algorithm (i.e., the same algorithm described above) which includes a convenient number of EEG epochs to emphasize ECR; (d) adjusting electrical stimulation current level to obtain ECR on the intracochlear electrode array (e.g., 122, 222) for a desired minimum external sound intensity level; (e) establishing a threshold or minimum level of the stimulation electrical current necessary to get ECR on each intracochlear electrode; (f) establishing the maximum or comfort level of the stimulation electrical current base on its threshold or minimum level; and (g) reporting the operational parameters of functional intracochlear electrodes and number and position of the non-functional intracochlear electrodes.

Figure 5:
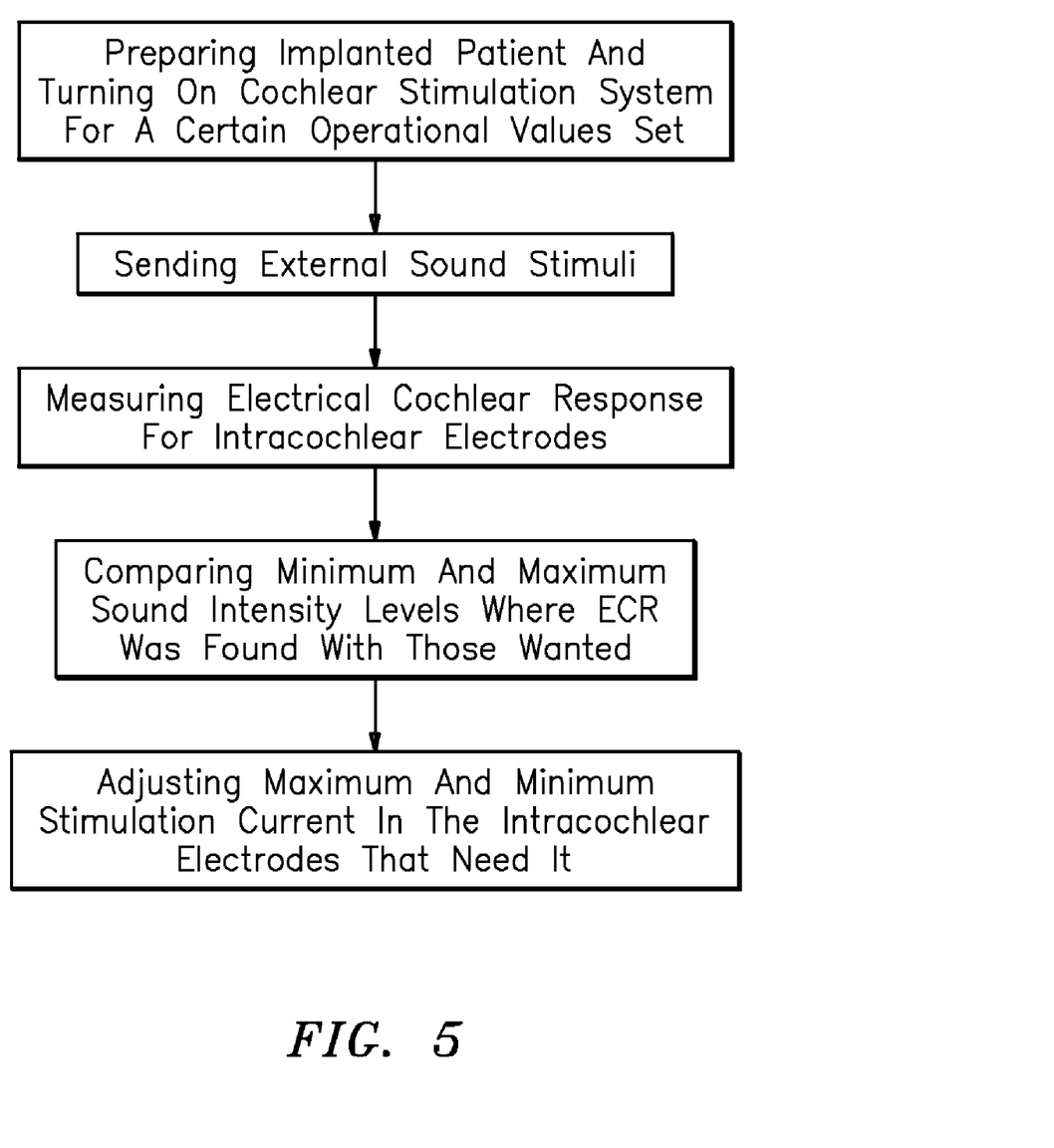
FIG. 5 shows a flowchart depicting the steps traversed to calibrate the implanted patient's Cochlear Stimulation System, according to the present invention.

FIG. 5 is a flowchart depicting a method for calibrating a Cochlear Stimulation System based on the Electrical Cochlear Response measurement, according to the present invention. The preferred "calibration" method steps comprise: (a) preparing the patient (e.g., 106, 206) by placing the register electrode system (e.g., 102, 202) on the scalp and turning on the Cochlear Stimulation System for an initial operational parameter values set and leading the implanted patient (e.g., 106, 206) afterwards into the calibrated sound field; (b) presenting variable duration, intensity level and frequency external sound stimuli within a suitable and comfortable dynamic range; (c) obtaining and measuring the resulting ECR due to the external sound stimuli presentation to the implanted patient (e.g., 106, 206); (d) comparing minimum and maximum sound intensity levels of the sound stimulus where ECR was found with those considered desirables for the implanted patient; and (e) readjusting the maximum and minimum values of the stimulation electrical current for those intracochlear electrode array (e.g., 122, 222) where a meaningful difference between the intensity level of the external sound stimulus for ECR detection and the desired intensity level of the same is found.

Figure 6:
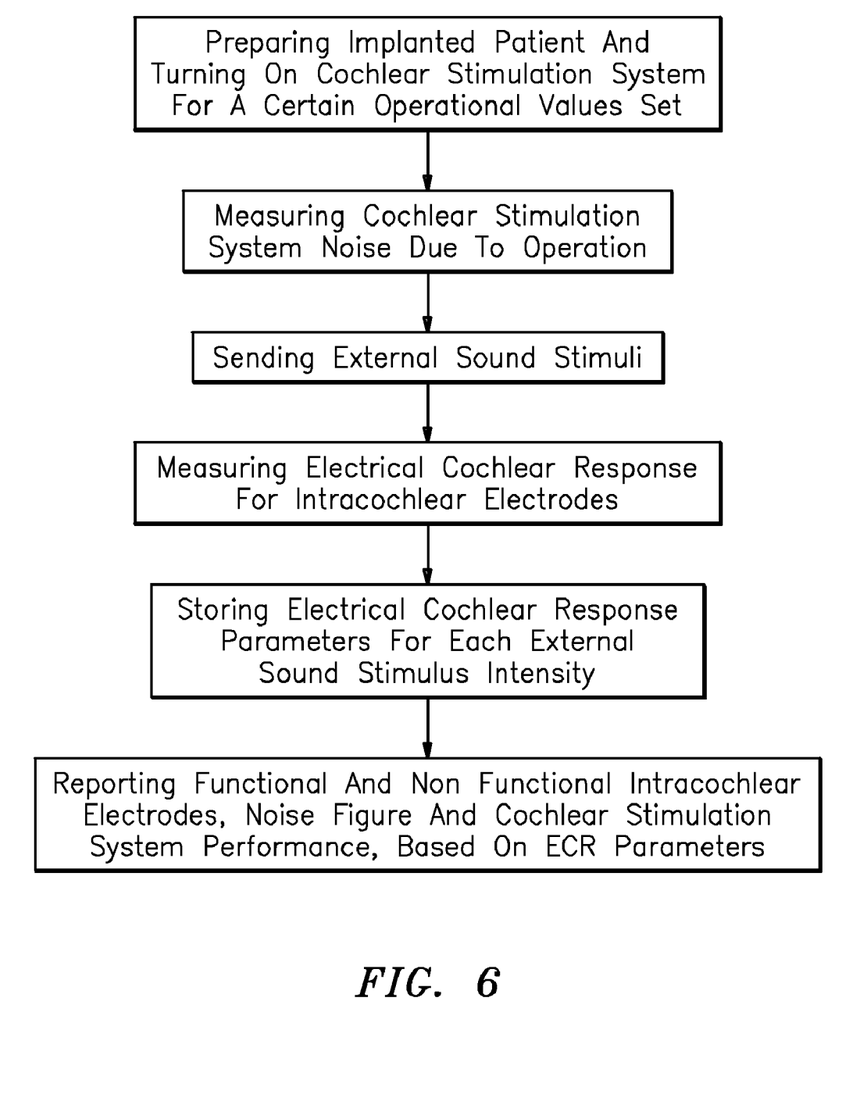
FIG. 6 shows a flowchart depicting the steps traversed to make a performance evaluation and failure detection of the implanted patient's Cochlear Stimulation System, according to the present invention.

FIG. 6 is a flowchart depicting a method for evaluation and failure detection of a Cochlear Stimulation System based on the measure of the Electrical Cochlear Response, according to the present invention. The preferred "evaluation and failure detection" method steps comprise: (a) preparing the patient (e.g., 106, 206) by placing the register electrode system (e.g., 102, 202) on the scalp and turning on the Cochlear Stimulation System (e.g., 114, 214) for an initial operational parameter values set (i.e., the number of channels or frequency bands in which the input sound is separated; sound processor gain and sensibility; the intracochlear electrode associated to each frequency band and the electrical stimulation current dynamic range for each intracochlear electrode) and leading the implanted patient (e.g., 106, 206) afterwards into the calibrated sound field; (b) measuring Cochlear Stimulation System (e.g., 114, 214) noise level due to operation without any external input sound; (c) presenting variable duration, intensity level and frequency external sound stimuli within a suitable and comfortable dynamic range; (d) obtaining and measuring the resulting ECR due to the external sound stimuli presentation to the implanted patient (e.g., 106, 206); (e) obtaining and storing of the ECR's measured parameters along with frequency and intensity level of the external sound stimulus; and (f) reporting functional and non-functional intracochlear electrodes, noise level and Cochlear Stimulation System performance, based on the ECR parameter values.

Figure 7:
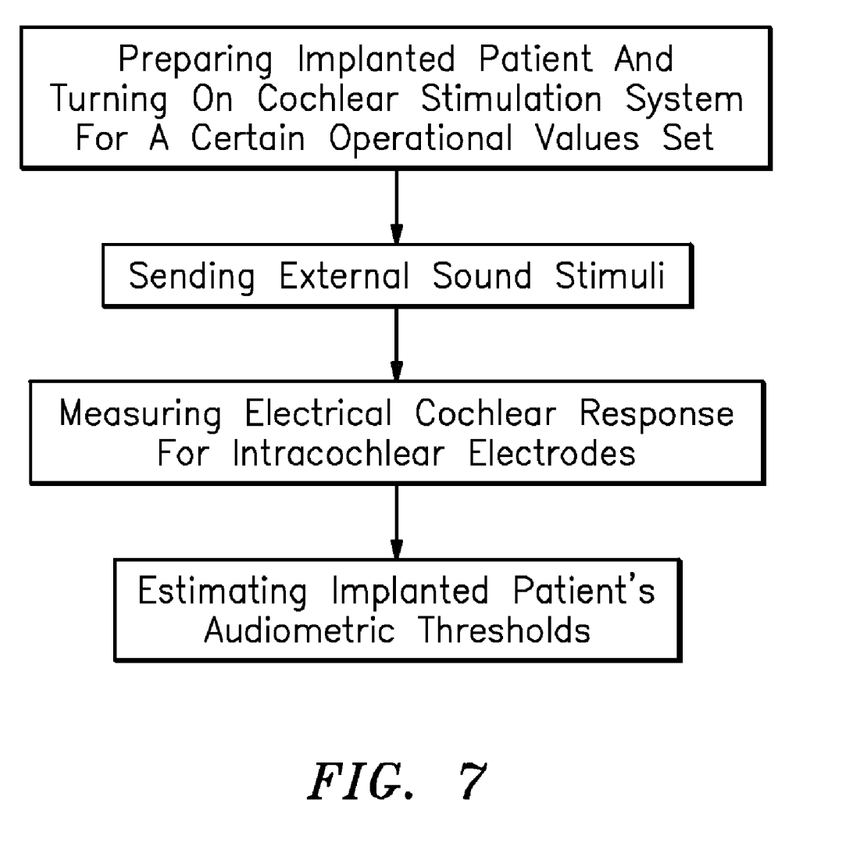
FIG. 7 shows a flowchart depicting the steps traversed to make an implanted patient's audiometric thresholds estimation, according to the present invention.

FIG. 7 is a flowchart depicting a method for audiometric threshold estimation of the implanted patient based on the measure of the Electrical Cochlear Response, according to the present invention. The preferred "threshold" method comprises: (a) preparing the patient (e.g., 106, 206) by placing the register electrode system on the scalp and turning on the Cochlear Stimulation System (e.g., 114, 214) for an initial operational parameter values set and leading the implanted patient (e.g., 106, 206) afterwards into the calibrated sound field; (b) presenting variable duration, intensity level and frequency external sound stimuli within a suitable and comfortable dynamic range; (c) obtaining and measuring the resulting ECR due to the external sound stimuli presentation to the implanted patient; and (d) estimating audiometric thresholds of the implanted patient (e.g., 106, 206) based on the minimum external sound intensity necessary for an ECR's parameters measure.

Figure 8:
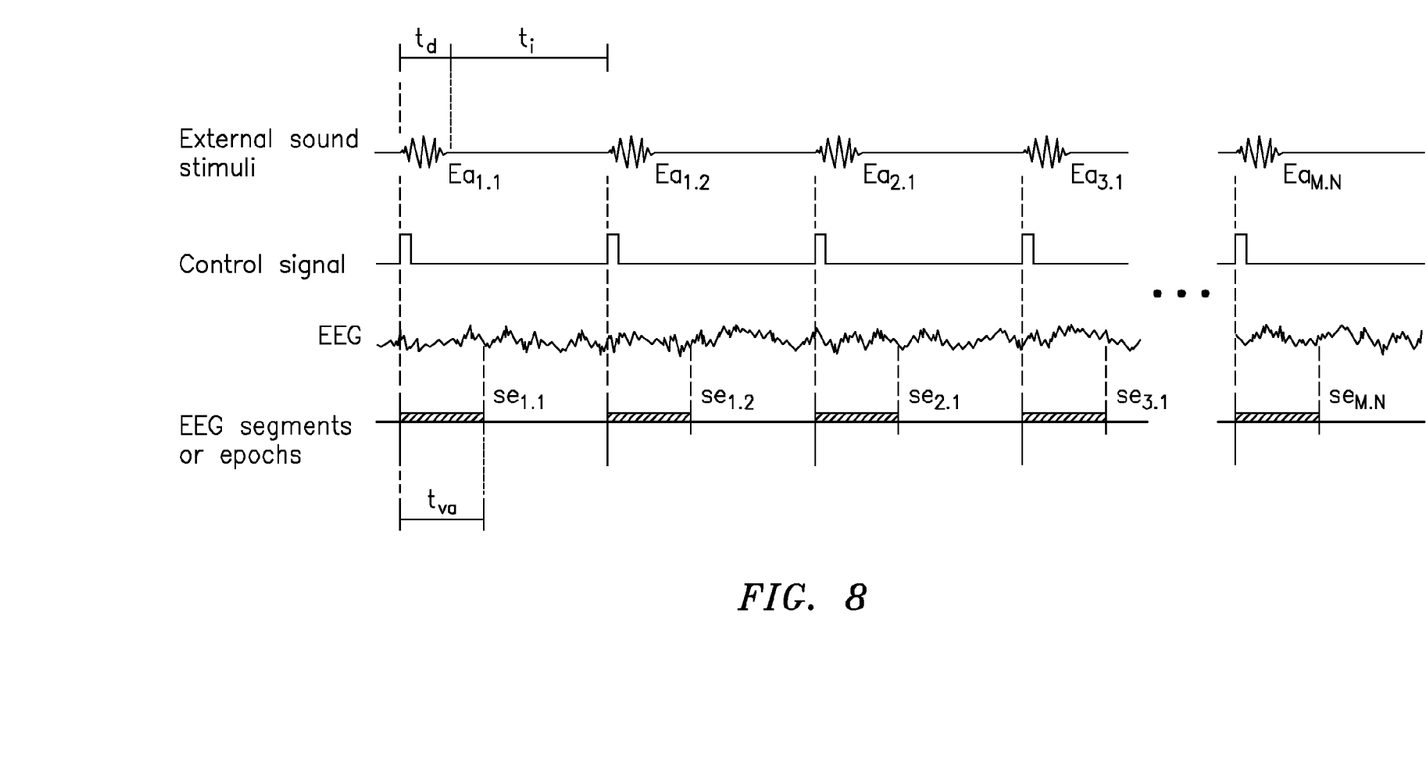
FIG. 8 is a graph showing the time relationship between the external sound stimuli presentation and the acquired EEG epochs used in the averaging algorithm to obtain ECR.

FIG. 8 is a graph showing the time relationship between the external sound stimuli presentation and the acquired EEG epochs used in the averaging algorithm to obtain ECR. In this graph: Ea=external sound stimulus; IS (not designated)= sound intensity or sound pressure level; M=number of epoch per electrode/frequency; N=number of electrodes; j=1 . . . , M; k=1 . . . , N; $se_{(M,N)}$=EEG segment or epoch captured for each Ea(j, k) @ IS of the external sound stimuli; $t_d$=sound stimuli duration; $t_t$=time between two consecutive sound stimuli; and $t_{va}$=analysis window.

Audiometric measurements are normally made in dB HL ("Hearing Level" decibels also expressed sometimes as $dB_{HL}$). They are a measure of a person's audition level in the frequency range of the human communication. The $dB_{HL}$ scale is a linearization of the frequency response curve of the human ear to frequency of a sound. Technically 0 $dB_{HL}$ for certain audio frequency corresponds to the minimum sound pressure level expressed in $dB_{SPL}$ re: 20 µPa, required for a person to hear a given frequency (i.e., 0 $dB_{HL}$@125 Hz=47.7 $dB_{SPL}$; 0 $dB_{HL}$@1000 Hz=7 $dB_{SPL}$; ISO 389-3:1994).

Figure 9:
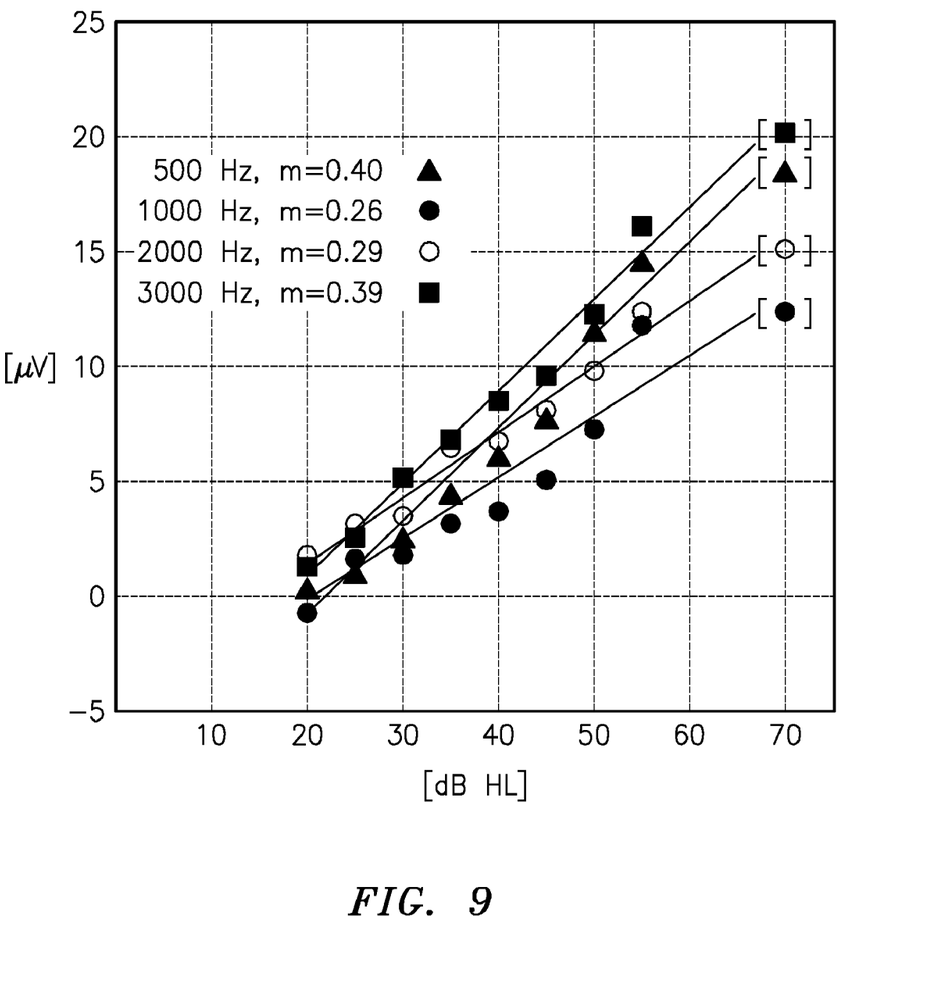
FIG. 9 is a graph of ECR amplitude growth function for four intracochlear electrodes of the implanted patient's Cochlear Stimulation System, according to the present invention.

FIG. 9 shows a graph representing the input-output relation of the ECR amplitude, B-C peak difference, versus external intensity sound stimulation, for four different frequencies. In this graph the Y-axis or amplitude is measured in micro volts ("µV") and the X-axis is in hearing level decibels ("$dB_{HL}$"). This graph shows an example of the ECR's Amplitude Growing Function versus external sound stimulus intensity level expressed in $dB_{HL}$ for four different frequencies (i.e., 500, 1000, 2000 and 3000 Hz). The regression straight line for each frequency is the best fitting curve for the experimental data. Positive slopes ("m") (i.e., m=0.40 @ 500 Hz, m=0.26 @ 1000 Hz m=0.29 @ 2000 Hz and m=0.39 @ 3000 Hz) shows ECR amplitude increasing as external sound intensity increases.

Figure 10:
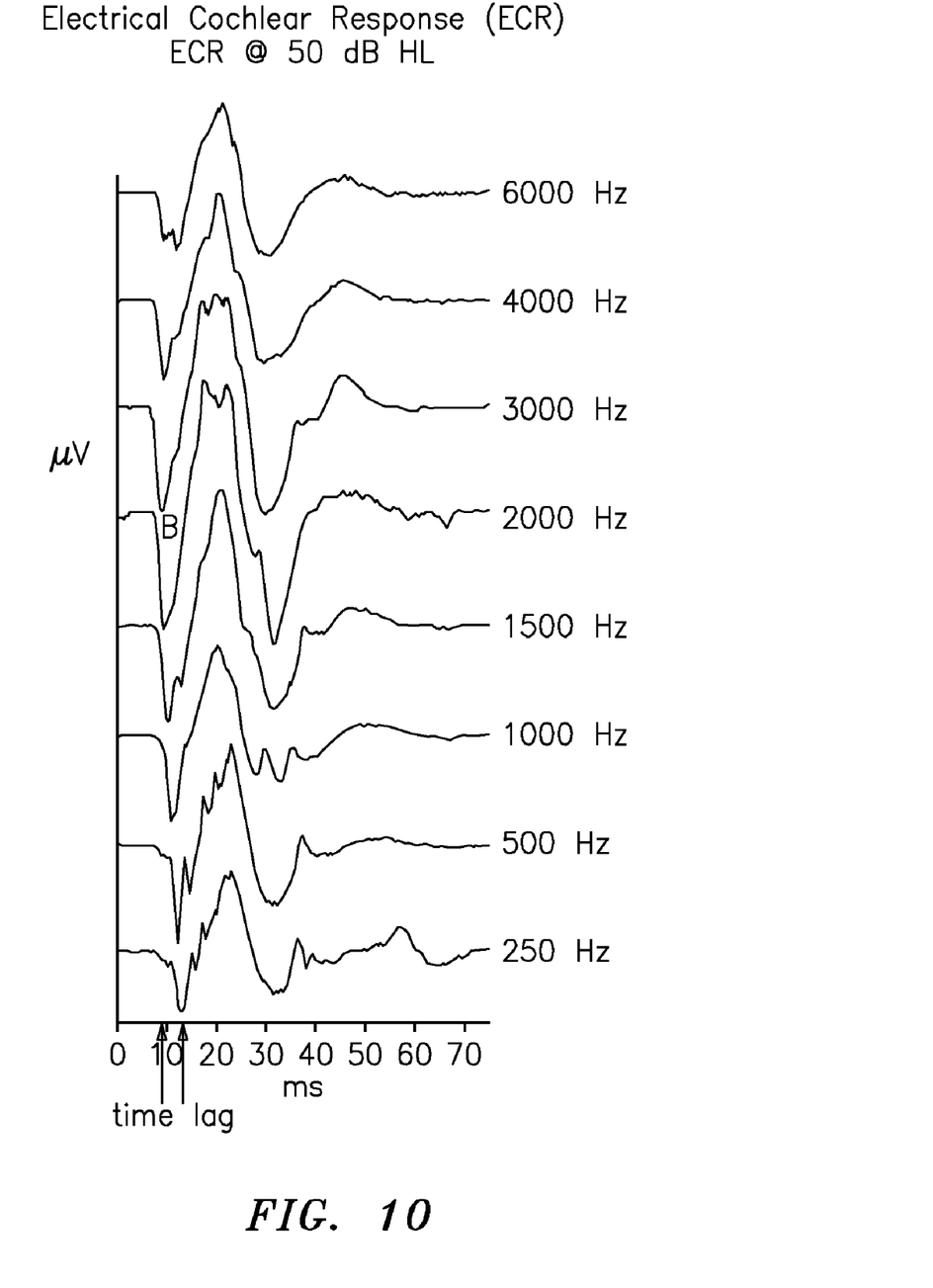
FIG. 10 is a graph showing the ECR time lag, particularly of the negative peak B, versus external sound stimulus frequency according to this invention.

FIG. 10 depicts a typical waveform family of the ECR of a same implanted patient, for a short time duration external sound stimulation of 50 dB HL, from 250 to 6,000 Hz; showing an ECR time lag as the frequency of the external sound stimulation is decreased. Particularly, it shows the time lag, measured in milliseconds ("ms"), of the negative peak B at various frequencies.

In a sense, Applicants' preferred apparatus set-ups 100 and 200 can be thought of as registration and measurement means for objectively obtaining ECR of an implanted patient with a Cochlear Implant, without the conscious participation of the implanted patient, by registering EEG activity from a far-field electrical potential registered on the scalp of the patient and measuring the EEG activity via an averaging algorithm.

It should be understood by those skilled in the art that obvious modifications can be made to Applicants' disclosed apparatus and method without departing from the spirit or scope of the invention. The illustrated embodiments are just examples, and there might be some other derivatives of their parameter combinations or from the relation of the same with other operation parameters of the Cochlear Stimulation System. Some examples of other parameters are the width, symmetry, elapsed time between positive and negative phases, and stimulation rate of the current stimulation biphasic pulse; also the applied algorithm for codification of input sound into electrical current pulses and the stimulation strategy used (e.g., CIS, ACE, SPEAK). Accordingly, reference should be made primarily to the appended claims rather than the foregoing description and drawings to determine the scope of the invention.

We claim:

1. An apparatus for obtaining an electrical cochlear response ("ECR") of a patient using a cochlear stimulation system, the apparatus comprising:
a sound generating system for generating an external sound stimulus to the cochlear stimulation system;
an electro encephalographic (EEG) acquisition system for registering EEG electrical activity generated when the external sound is processed by the cochlear stimulation system; and
a computer-controlled system having hardware and software configured to:
receive the EEG activity as EEG epochs corresponding to a repeated sound stimulation, the EEG epochs having a time sufficient for at least one waveform; and
averaging software configured to average a plurality of EEG epochs to generate the ECR where the ECR is characterized by an ECR waveform having parameters that measure the patient's objective perception of the external sound.

2. The apparatus of claim 1 where the sound generating system includes:
a signal generator for generating stimulation signals;
an amplifier for amplifying the stimulation signals; and
an electroacoustic transducer coupled to the amplifier for providing the patient with the external sound stimulus.

3. The apparatus of claim 1 where the EEG acquisition system includes a register electrode system placed on the scalp of the implanted patient for picking up the implanted patient's EEG activity.

4. The apparatus of claim 1 further comprising an audiometric enclosure in which the implanted patient is housed.

5. The apparatus of claim 1 further comprising a reduced dimension test sound chamber in which the electroacoustic transducer is mechanically coupled to a microphone of the cochlear stimulation system.

6. A method for obtaining an electrical cochlear response ("ECR") of an implanted patient with a cochlear stimulation system comprising:
generating an external sound stimulus at a predetermined dynamic range;
registering EEG activity arising from the external sound stimuli, the EEG activity detected from electrical signals registered on the scalp of the patient; and
processing the EEG activity as EEG epochs corresponding to a repeated sound stimulation; and
averaging a plurality of EEG epochs to generate the ECR where the ECR is characterized by an ECR waveform having parameters that measure the patient's objective perception of the external sound.

7. The method of claim 6 further comprising:
before the step of registering EEG activity, mounting a register electrode system on the scalp of the patient.

8. The method of claim 6 further comprising fitting the cochlear stimulation system by a method comprising:
controlling the cochlear stimulation system to operate according to an initial set of operational parameter values;
after the step of processing the EEG activity to obtain the ECR, adjusting the operational parameters of the cochlear stimulation system according the ECR parameters obtained from the register electrode system;
setting the dynamic range of the electrical stimulation current level for the intracochlear electrodes; and
reporting the operational parameters of the intracochlear electrodes.

9. The method of claim 8 further comprising:
setting the initial operational parameter values to be one or more of: the number of frequency bands in which the input sound is separated, sound processor gain and sensibility, the intracochlear electrode associated to each frequency band and the electrical stimulation current dynamic range for each intracochlear electrode.

10. The method of claim 6 further comprising calibrating the cochlear stimulation system by a method comprising:
before the step of registering EEG activity, controlling the cochlear stimulation system with an initial set of operational parameters with values determined to set the cochlear stimulation system according to daily conditions of the implanted patient; and
after the step of processing the EEG activity to obtain the ECR, adjusting the dynamic range of the electrical stimulation current level for the intracochlear electrodes according to the ECR parameters obtained from measuring the ECR.

11. The method of claim 10 further comprising:
setting the initial operational parameter values to be one or more of: the number of frequency bands in which the input sound is separated, sound processor gain and sensibility, the intracochlear electrode associated to each frequency band and the electrical stimulation current dynamic range for each intracochlear electrode.

12. The method of claim 6 further comprising performing an evaluation and failure detection method comprising:
before the step of registering EEG activity, controlling the cochlear stimulation system to operate using an initial set of operational parameter values;
after the step of processing the EEG activity, storing the ECR's measured parameters; and
reporting noise levels, non-functional intracochlear electrodes and performance of the cochlear stimulation system, based on the ECR parameter values.

13. The method of claim 12 further comprising:
setting the initial operational parameter values to be one or more of: the number of frequency bands in which the input sound is separated, sound processor gain and sensibility, the intracochlear electrode associated to each frequency band and the electrical stimulation current dynamic range for each intracochlear electrode.

14. The method of claim 6 further comprising estimating the audiometric thresholds of the implanted patient by a method comprising:
controlling the cochlear stimulation system to operate using an initial set of operational parameter values; and
after the step of processing the EEG activity, estimating audiometric thresholds of the implanted patient based on the minimum external sound intensity necessary for ECR detection in corresponding intracochlear electrodes.

* * * * *